(12) United States Patent
Hedberg

(10) Patent No.: US 7,416,529 B2
(45) Date of Patent: Aug. 26, 2008

(54) DETECTION OF DIASTOLIC HEART FAILURE

(75) Inventor: Sven-Erik Hedberg, Kungsängen (SE)

(73) Assignee: St. Jude Medical AB, Jarfalla (SE)

( * ) Notice: Subject to any disclaimer, the term of this patent is extended or adjusted under 35 U.S.C. 154(b) by 256 days.

(21) Appl. No.: 10/562,181

(22) PCT Filed: May 13, 2004

(86) PCT No.: PCT/SE2004/000741

§ 371 (c)(1),
(2), (4) Date: Dec. 22, 2005

(87) PCT Pub. No.: WO2005/110535

PCT Pub. Date: Nov. 24, 2005

(65) Prior Publication Data

US 2006/0149155 A1 Jul. 6, 2006

(51) Int. Cl.
*A61B 1/00* (2006.01)
(52) U.S. Cl. .......................................... 600/485; 607/23
(58) Field of Classification Search ................. 600/485, 600/486, 500; 607/9, 23
See application file for complete search history.

(56) References Cited

U.S. PATENT DOCUMENTS 6,438,408 B1 8/2002 Mulligan et al.

(Continued)

FOREIGN PATENT DOCUMENTS

EP 1 348 375 10/2003

(Continued)

OTHER PUBLICATIONS

"Mechanisms, Diagnosis, and Treatment of Diastolic Heart Failure," Lenihan et al, American Heart Journal, vol. 130 (1995) pp. 153-166.

(Continued)

*Primary Examiner*—Scott M Getzow
(74) *Attorney, Agent, or Firm*—Schiff Hardin LLP (57) ABSTRACT

An implantable medical apparatus for detecting diastolic heart failure, DHF, has a DHF determining device for determining at least one blood pressure parameter for detecting a DHF state of the heart of a patient. The DHF determining device has a pressure measuring unit for measuring the absolute value of left atrial pressure during the diastasis phase just before atrial contraction, or the absolute value of the pressure in the pulmonary vein when the pulmonary valve is closed, for a predetermined workload situation and a rest situation of the patient. A comparator compares the difference between left atrial pressure or pulmonary vein pressure, in the workload and rest situations, with a predetermined pressure difference reference value. A pacemaker includes such an apparatus and a control unit that optimizes pacing therapy depending on the result of the comparisons with the reference values. In a corresponding method of detecting diastolic heart failure, DHF at least one blood pressure parameter for detecting a DHF state of the heart of a patient is determined. The absolute value of left atrial pressure is measured during the diastasis phase just before atrial contraction, or the absolute value of the pressure in the pulmonary vein when the pulmonary valve is closed, for a predetermined workload situation and a rest situation of the patient. The difference between left atrial pressure or pulmonary vein pressure in said workload and rest situations is compared with a predetermined pressure difference reference value.

23 Claims, 5 Drawing Sheets

U.S. PATENT DOCUMENTS

2003/0045800 A1    3/2003    Noren et al.

FOREIGN PATENT DOCUMENTS

WO    WO 01/36014    5/2001

OTHER PUBLICATIONS

"Pathophysiological Characterization of Isolated Diastolic Heart Failure in Comparison to Systolic Heart Failure," Kitzman et al, Journal of the American Medical Association, vol. 288, No. 17 (Nov. 6, 2002) pp. 2144-2150.

DETECTION OF DIASTOLIC HEART FAILURE

BACKGROUND OF THE INVENTION

1. Field of the Invention

The present invention relates to an implantable medical apparatus for detecting diastolic heart failure (DHF), of the type having a DHF determining device for determining at least one blood pressure parameter for detecting a DHF state of the heart of a patient. The invention also relates to a pacemaker provided with such an apparatus, and a method of detecting DHF, including the step of determining at least one blood pressure parameter for detecting a DHF state of the heart of a patient.

2. Description of the Prior Art

There is a growing recognition that congestive heart failure caused by a predominant abnormality in the diastolic function, i.e. diastolic heart failure, DHF, is both common and causes significant morbidity and mortality. Therefore early detection of DHF is important. Patients do not, however, seem to have symptoms at an early stage. In addition it has been hard to separate diastolic and systolic heart failure and they may also exist simultaneously.

It has been discovered that among the few parameters, separating diastolic heart failure from systolic heart failure, are certain blood pressure parameters obtained during work of the patient. Thus U.S. Pat. No. 6,438,408 describes an implantable medical device for monitoring congestive heart failure, CHF. A number of heart failure parameters indicative of the state of the heart failure are measured employing EGMs, blood pressures including absolute pressures, developed pressures (=systolic pressures−diastolic pressures) and the time derivative dP/dt, as well as heart chamber volumes. One of these parameters is the relaxation or contraction time constant $\tau$ of the heart chamber. This constant $\tau$ is calculated from a continuous pressure signal and is the drop in ventricular pressure at the end of systole and in the first part of diastole. The $\tau$ parameter is thus a general parameter reflecting the relaxation process.

Figure 1A:
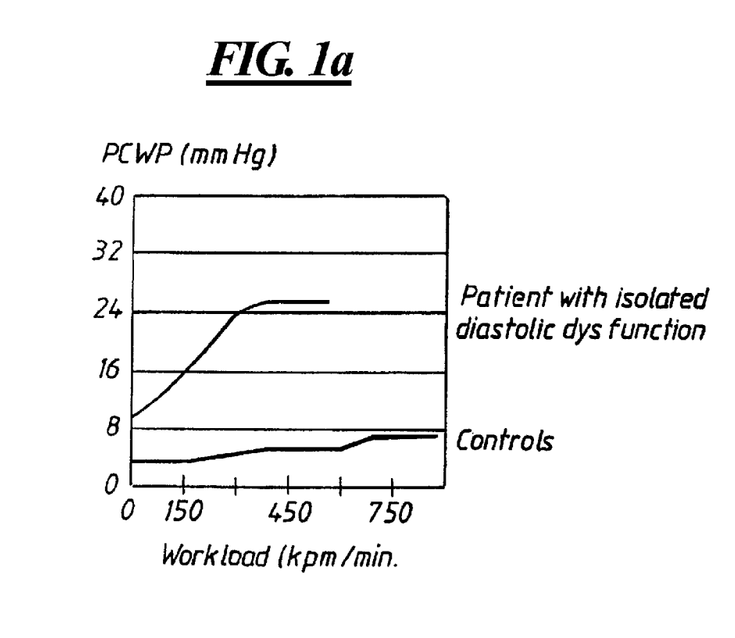
FIGS. 1a and 1b are diagrams showing PCWP and LVEDVI, respectively, as functions of workload for patients having a diastolic disfunction and control persons not suffering from this disfunction.
Figure 1B:
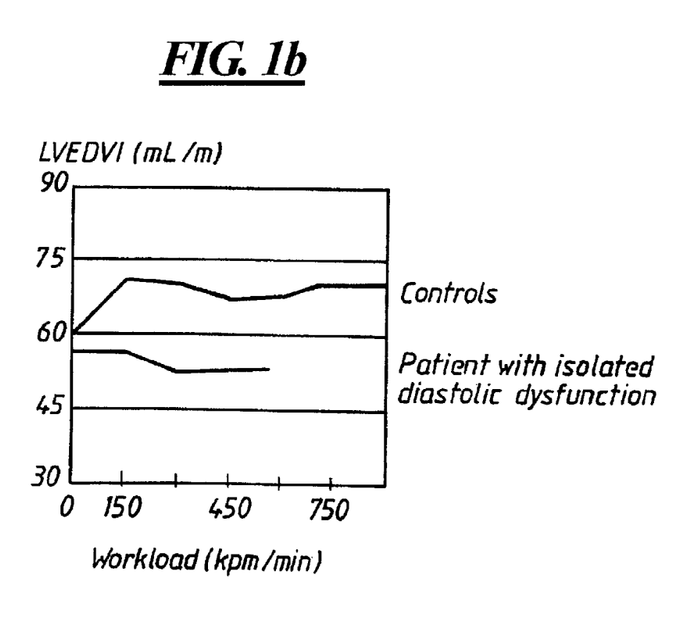

Patients suffering from DHF have both elevated ventricular filling pressure and elevated pulmonary venous pressure. To maintain cardiac output under load higher filling pressures are required to achieve adequate left ventricular filling, see H. Weinberger, Diagnosis and Treatment of Diastolic Heart Failure, Hospital Practice, http://www.hosppract.com/issues/1999/03/weinb.htm. However, for DHF patients increased filling pressure does not result in increased left ventricular diastolic volymes. This is illustrated in FIG. 1 which shows results of studies on patients with isolated diastolic dysfunction, see D. W. Kitzman et al, "Exercise Intolerance in Patients with Heart Failure and Preserved Left Ventricular Systolic Function: Failure of the Frank-Starling Mechanism", J. Am. Coll. Cardiol., 17:1065-1072, 1991. FIG. 1a shows the pulmonary capillary wedge pressure, PCWP, as a function of workload for patients with isolated diastolic dysfunction and for control persons not suffering for this dysfunction, and FIG. 1b shows corresponding curves for the left ventricular end-diastolic volume index, LVEDVI as a function of the workload. From the figures it appears that for patients suffering from the mentioned diastolic dysfunction, PCWP was elevated at rest and further elevated during exercise. This indicates that the ventricular filling pressure was increased under both conditions, whereas LVEDVI did not increase with exercise.

SUMMARY OF THE INVENTION

An object of the present invention is to utilize the above information to provide a technique for detecting DHF based on measurement of left atrial or pulmonary vein pressure.

Thus with the present invention the reduced peak and submaximal exercise performance of DHF patients are utilized for detecting DHF. With a sensor placed in left atrium or very close to the endocardium thereof, the left atrial pressure is measured during the diastasis phase just before atrial contraction. Alternatively a sensor in the pulmonary vein can be used, provided that pressure data for subsequent analysis are collected only when the pulmonary valve is closed. With the technique according to the invention it is possible to detect DHF at an early stage, often before the patient seems to have any symptoms.

In the present invention the workload situation of the patient must be identified, and therefore, in an embodiment of the apparatus according to the invention, an activity sensor is provided for determining the workload of the patient.

Since the absolute pressure is used, measured pressure values must be corrected with e.g. the level of the mean pressure in the right atrium or in vena cava close to the right atrium. This correction is needed because any column of blood above the sensor location, which thus is posture depending, will add to the absolute pressure level. Such a correction will also compensate for a varying ambient pressure. In an embodiment of the apparatus according to the invention a pressure compensator is therefore provided for correcting the measured absolute value of left atrial pressure with the mean (average) pressure in right atrium or in vena cava close to the right atrium.

In another embodiment of the apparatus according to the invention the DHF determining device includes an impedance measuring unit for measuring the impedance between a left ventricular electrode and a second electrode intended to be positioned at a location so that most of variations in the measured impedance are due to varying left ventricular volume. $\Delta P$ values and corresponding values of the difference, $\Delta V$, in the end-diastolic ventricular volume, obtained from the impedances measured for the predetermined workload situation and for the patient in rest are supplied to a quotient forming unit to form the quotient $\Delta P/\Delta V$, and a comparator compares this said quotient $\Delta P/\Delta V$ with a predetermined quotient reference value for DHF detection. By adding information about left ventricular end-diastolic pressure the DHF detection can be improved. In a healthy person the end-diastolic volume increases with exercise but shows only a small increase in left atrial pressure. In a person suffering from DHF, who has a more stiff heart muscle, the left ventricular end-diastolic volume changes very little but there is a large increase in left atrial pressure. The quotient $\Delta P/\Delta V$ is consequently a useful quantity for improving the detection of DHF. The difference $\Delta V$ is determined by impedance measurements.

In other embodiments of the apparatus according to the invention, a first averaging unit forms an average value of the absolute pressures measured during a of cardiac cycles with the predetermined workload situation and an average value of the absolute pressures measured during a number of cardiac cycles with the patient in rest, and a second averaging unit forms an average value of the impedance measured during a number of cardiac cycles with the predetermined workload situation and an average value of the impedance measured during a number of cardiac cycles with the patient in rest. In this way the quality of the pressure measurements as well as the impedance measurements are improved.

In other embodiments of the apparatus according to the invention a wireless communication unit is connected to the comparator for automatically sending the results of the comparisons with the reference values to an external receiver, or a memory is provided for storing the results of the comparisons with the reference values. Thus if the measured absolute pressure, and possibly also the quotient $\Delta P/\Delta V$, have risen above the associated reference values in a predetermined way, this condition is automatically transmitted to a physician or stored for transmission in connection with a follow-up.

The invention also relates to a pacemaker provided with the apparatus for detecting DHF and a control unit that optimizes pacing therapy depending on the result of the comparisons with the predetermined reference values. The pressure measuring unit of the apparatus according to the invention then preferably is a pressure sensor connected to the pacemaker, since it can monitor the pulse pressure of its carrier for long periods. This is an advantage since evolvement of DHF is a slow process.

In an embodiment of the pacemaker according to the invention, a rate responsive sensor is used as an activity sensor for determining the workload situation of the patient. Even the pressure sensor of the pacemaker can be used as activity sensor.

In an embodiment of the method according to the invention in a calibration procedure instantaneous values of the left ventricular volume are measured by an ultrasound technique and the relation is established between these measured ventricular volume values and simultaneously measured impedance values. Since the measured impedance depends on the location of the electrodes used, it will vary from patient to patient and therefore such a calibration is required.

As mentioned above the measured difference between left atrial pressure measured in workload and rest situations is compared with a predetermined pressure difference reference value. The reference value for detection of DHF is preferably obtained from measurements on the patient at an early stage of the implantation period of the apparatus or pacemaker. The patient is assumed not to suffer from DHF at the time of implantation. Therefore, in an embodiment of the method according to the invention, the pressures are measured for different workloads of the patient and for the patient in rest at an early time, when the patient is not suffering from DHF, for determining the pressure difference reference value. Corresponding impedance measurements are preferably also made on the patient at this early stage for determination of the quotient reference value.

DESCRIPTION OF THE PREFERRED EMBODIMENTS

FIGS. 1a and 1b show results of studies on patients having a diastolic dysfunction as explained above. From these figures it can be seen that a heart suffering from DHF has another PCWP versus workload behaviour than a normal heart, "Controls" in the figure. The present invention is based on this knowledge since the PCWP is approximately equal to the left atrial pressure LAP.

Figure 2:
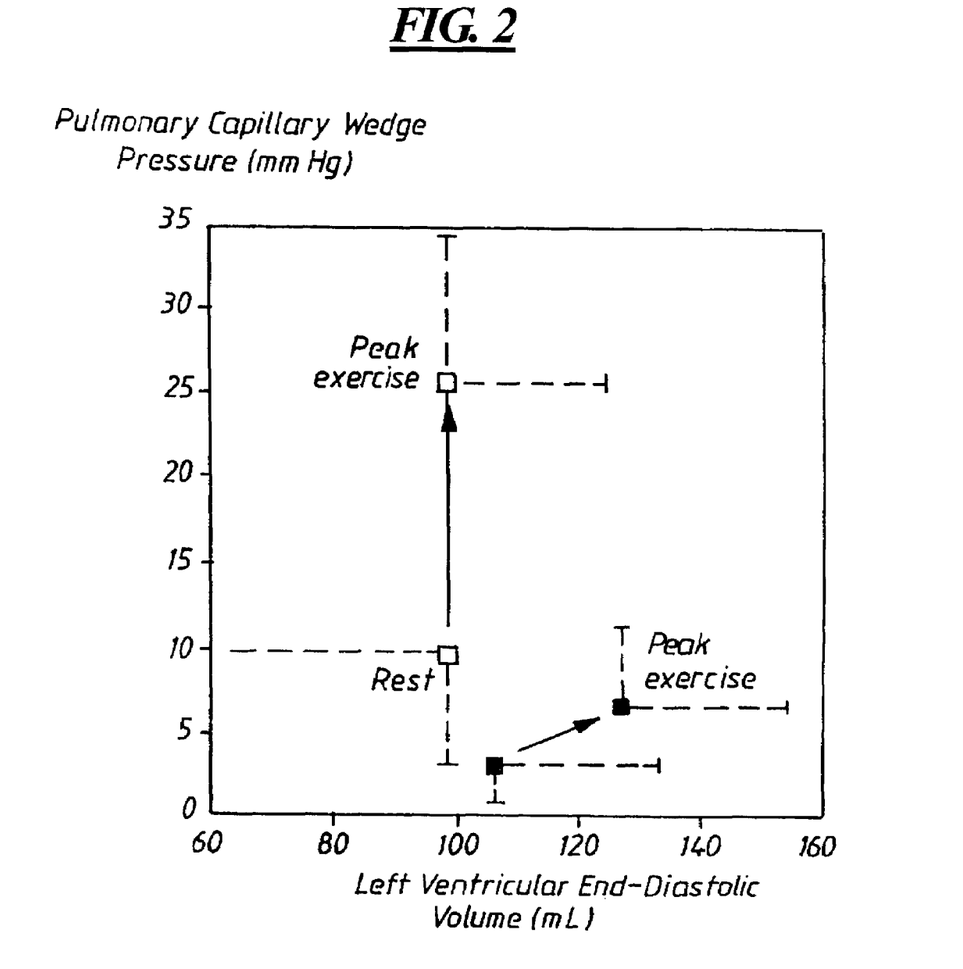
FIG. 2 is a plot of PCWP versus left ventricular end diastolic volume.

The detection of DHF by measurements of the absolute left atrial pressure LAP or the pressure in the pulmonary vein can be improved by adding information about left ventricular end-diastolic volume. In a healthy person the end-diastolic volume increases with workload or exercise, whereas the left atrial pressure shows only a small increase. In a person suffering from DHF the left ventricular end-diastolic volume changes vary little but there is a large increase in the left atrial pressure. This is illustrated by FIG. 2, which is a diagram from D. W. Kitzman et al, "Exercise Intolerance in Patients with Heart Failure and Preserved Left Ventricular Systolic Function: Failure of the Frank-Starling Mechanism", J. Am. Coll. Cardiol., 17:1065-1072, 1991, plotting PCWP versus left ventricular end-diastolic volume. The open boxes in the figure indicate the direction of change from rest to exercise or workload for patients with DHF, and the solid boxes illustrate the corresponding direction of change for normal control persons. The shift upwards in the diagram for non-healthy patients should be noted.

The left ventricular end-diastolic volume is preferably determined by measurements of the electric impedance between e.g. a left ventricular electrode, normally placed in a coronary vein, and an electrode in right ventricle, right atrium or any other place in or on the heart, such that most of the variations in the measured impedance derive from variations in the left ventricular volume, as will be described below.

The detection and measurement of degree of DHF can be improved by studying the quotient $\Delta P/\Delta V$. $\Delta P$ denotes the difference between left atrial pressure measured in the workload and rest situations and $\Delta V$ the difference in the end-diastolic ventricular volume, obtained by the impedances measurements, for the predetermined workload situation and for the patient in rest, as explained above.

The quantity $\Delta V$, and consequently the quotient $\Delta P/\Delta V$, is depending on the positions of the electrodes, used for the impedance measurements. These quantities will therefore vary from patient to patient. Thus some kind of calibration is needed.

The left ventricular volume varies during a cardiac cycle. The instantaneous volume can be measured by e.g. ultrasound technique. By simultaneously measuring corresponding impedance values a relation can be established between measured impedance values and left ventricular volume. The measured pressure difference $\Delta P$ can be directly obtained since the sensitivity of the pressure transducer is set by the manufacturer.

The reference value for the quotient $\Delta P/\Delta V$ for detection of DHF can be set from common knowledge about physiological properties during the progression of DHF. In the same way the severity of the progression of DHF can be followed.

Figure 3:
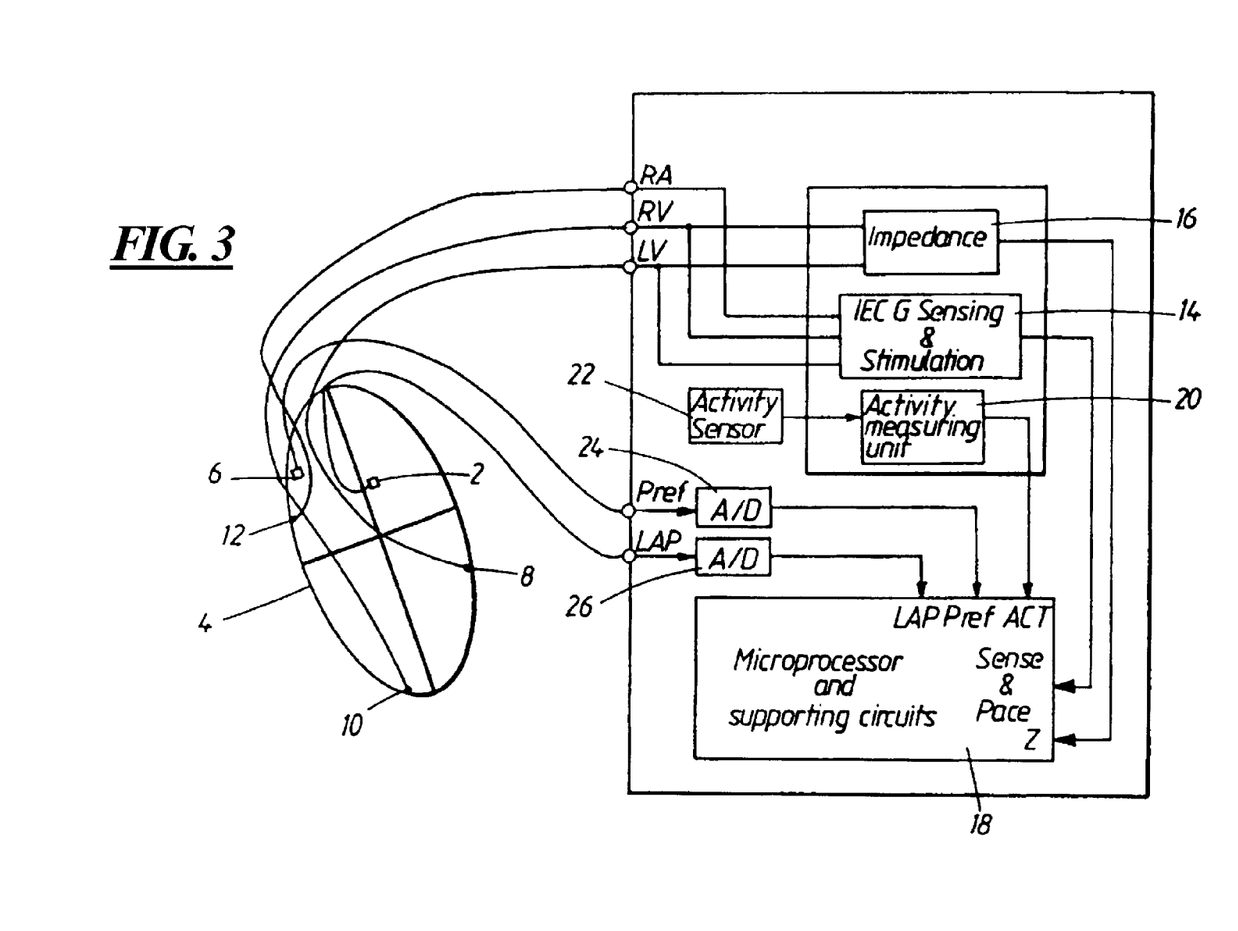
FIG. 3 is a block diagram of an embodiment of a pacemaker according to the present invention.

FIG. 3 is a block diagram of an embodiment of a pacemaker according to the invention, including a pressure sensor 2, sensitive to the pressure in left atrium, LAP, of a patient's heart 4. The atmospheric pressure and the pressure from blood volumes above the sensor also contribute to LAP. To compensate for this a sensor 6 is also provided for measuring the pressure in the right atrium or in vena cava. This compensation pressure is denoted by Pref.

A measurement value correlated to left ventricular volume changes ΔV is obtained by measuring the impedance Z between an electrode 8 in or attached to the left ventricle and an electrode 10 in the right ventricle. The parameters in question are measured in the diastasis phase just before the atrial contribution to the left ventricular filling. For this purpose a timer can be used, starting at the preceding contraction. Alternatively P-waves can be sensed by an electrode 12 implanted in the right atrium of the heart 4 for starting the measurement. Parameter values measured during a period preceding the atrial contraction are stored in a ring buffer. This procedure will be described below with reference to FIG. 4.

The pacemaker in FIG. 3 has ordinary circuits 14 for IEGM sensing and stimulation. It also comprises circuitry 16 for measuring the impedance Z between implanted electrodes 8, 10 as mentioned above. To determine volume changes of heart chambers by impedance measurements between electrodes implanted in the heart is per se previously known from e.g. EP 1 384 492. Such impedance measuring circuitry is also known from respiration activity measuring pacemakers.

The pacemaker illustrated in FIG. 3 also contains a unit 20 for measuring activity or workload of the patient by means of an activity or workload sensor 22. An ordinary microprocessor with supporting circuits 18 are provided for calculation and signal processing explained in the following with reference to FIGS. 4 and 5. Sensed Pref and LAP signals are digitized in A/D-converters 24 and 26 respectively before supplied to the microprocessor and supporting circuits 18. Data related to sensing and pacing, the measured impedance Z, and the activity or workload Act of the patient are supplied to the microprocessor and its supporting circuits 18 as well.

For communication with and transfer of data to external equipment the pacemaker is provided with a telemetry unit that is not shown in FIG. 3.

Figure 4:
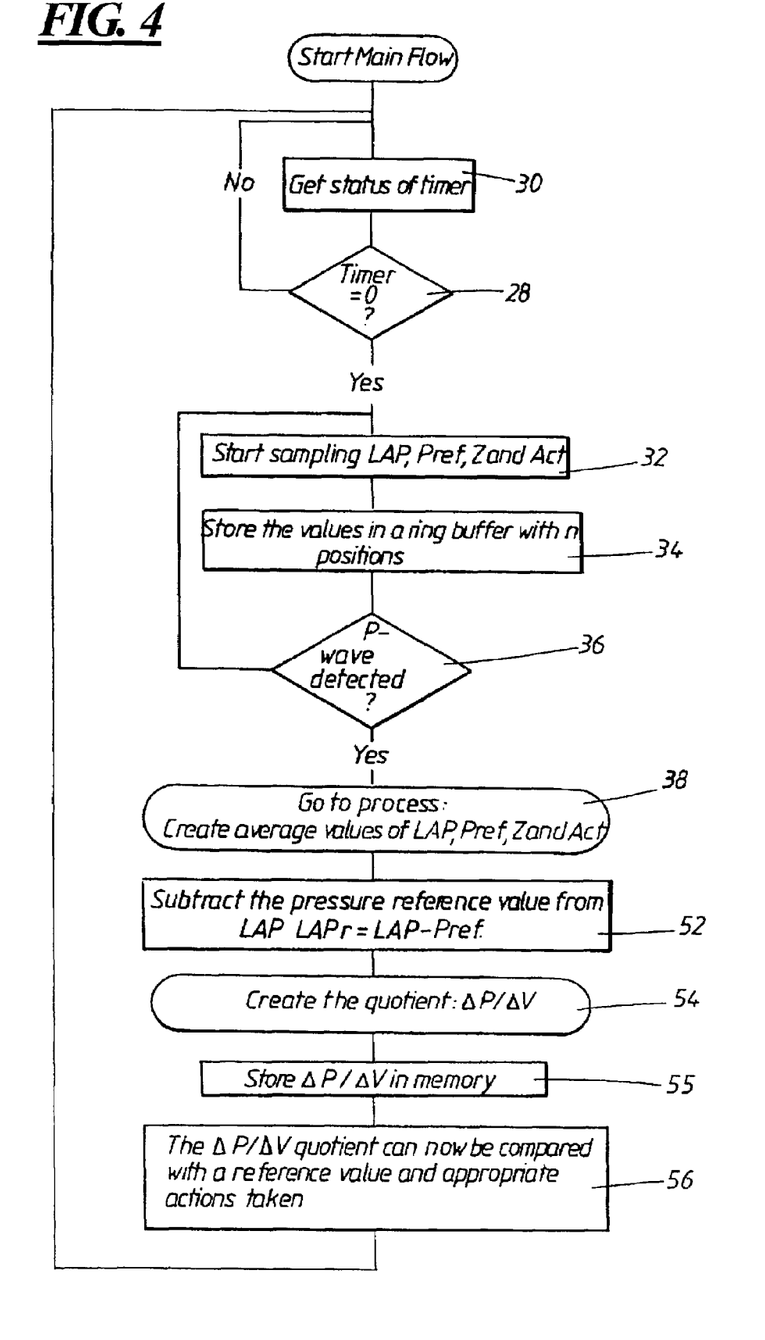
FIG. 4 is a flow chart illustrating a procedure for determination of the quotient $\Delta P/\Delta V$ in an embodiment of the apparatus according to the invention.

FIG. 4 illustrates the determination of the quotient ΔP/ΔV. Since DHF evolves slowly, necessary measurements may be performed regularly, preferably with long intervals, for a long time. A timer is therefore provided, block 28 in FIG. 4, and the process illustrated in the figure, is started by a check of status of the timer 28, block 30. The timer 28 may be set to e.g. hours, days or weeks.

As soon as the timer 28 has counted down to zero the measurements of LAP, Pref, the impedance Z corresponding to left ventricular volume, and the activity or workload Act of the patient are started, block 32 in FIG. 4. It should be noted that the impedance is inversely correlated to the volume, but since the impedance variations are small and superimposed on a larger absolute impedance, impedance measurements are anyhow suitable for this purpose.

Measured data are stored in a ring buffer with n positions and large enough to store data from pre-atrial loading of the left ventricle, block 34

As soon as a P-wave is detected, block 36, stored values of LAP, Pref, Z and Act are collected from a memory position n samples before the point of the P-wave detection. The number n depends on several circumstances, like the shape of the P-wave, the filter in the P-wave amplifier, and the position of the right atrial electrode 12. In this way data are obtained from a point of time immediately before a noticeable change of the ventricular volume caused by the atrial contribution.

Figure 5:
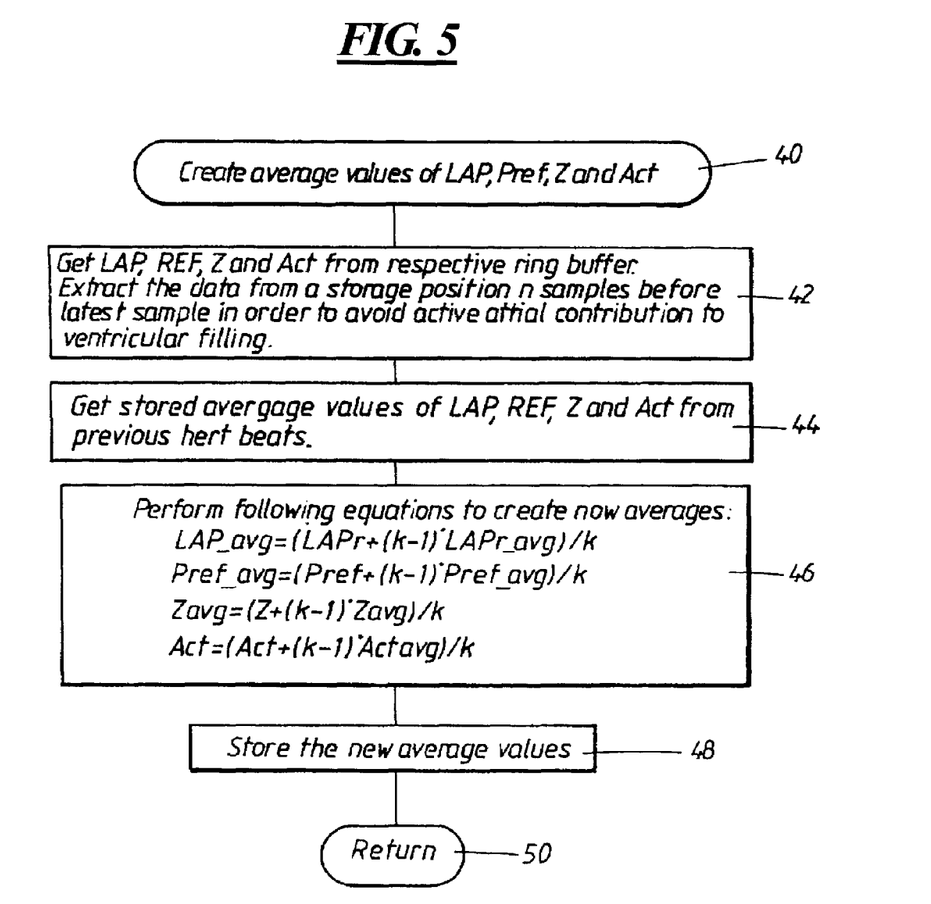
FIG. 5 is a flow chart illustrating an averaging process for the procedure illustrated in FIG. 4.

After this collection of parameter values average values of corresponding parameters, taken over several cardiac cycles, are created, block 38 in FIG. 4 and block 40 in FIG. 5. The average value creating process is illustrated in greater detail in FIG. 5. The purpose of the average creation is to improve the quality of data.

The contribution from the atrium to the ventricular filling should not be part of the left ventricular volume measured in this procedure, as explained above. Thus data are extracted from a storage position n samples before the latest sample, block 42 in FIG. 5, to avoid atrial contribution to the ventricular filling. Stored average values of LAP, Pref, Z and Act from previous heart beats are used, block 44, to produce a floating mean value by adding a fraction 1/k of the present value to the already existing "old" average value, according to the equation $$\text{New\_Average\_Value} = \frac{\text{Value} + (k-1) \cdot \text{Old\_Average\_Value}}{k}$$

where "Value" means the present value.

This process is performed for each of the parameters LAP, Pref, Z and Act, block 46, and the new average values are stored, block 48 in FIG. 5. Block 46 contains corresponding equations for creating new average values of each of the parameters LAP, Pref, Z and Act, "avg" denoting "average".

A return is then made, block 50, to the main procedure illustrated in FIG. 3, where the next step consists in subtraction of Pref from LAP to obtain the corrected LAP value $LAP_r$ as discussed above. Thus, $$LAP_r = LAP - Pref$$

block 52 in FIG. 4. The corrected value $LAP_r$ is then used to create the quotient ΔP/ΔV, block 54, store it in a memory, block 55, and compare the quotient ΔP/ΔV with a reference value for subsequent actions, block 56.

For this procedure the parameter values are preferably stored in an organized way, in this case in a table, see Table 1 below. This table is set up in a memory. The parameters are measured over time for different workload levels of the patient, and this is used to increase the number of available measurements to be used and to improve the results. When average values over several cardiac cycles of the parameters have been obtained $LAP_r$ and Z are stored in a table according to how actual activity or workload level fits the activity or workload intervals in the table. The following Table 1 shows an example of how this can be done.

TABLE 1

| Activity interval | $LAP_r$ | Z | Parameters set |
|---|---|---|---|
| $Act_1$ to $Act_2$ | Data | data | 1 |
| $Act_2$ to $Act_3$ | no data | no data | 0 |
| ... | ... | ... | ... |
| $Act_{n-1}$ to $Act_n$ | Data | data | 1 |
| N | | | Sum of above |

The table will contain very few data at the beginning of the use of the apparatus according to the invention. With every entry into this process data will be filled in the table, either directly or via an averaging process if data already exist in memory positions in question. An "1" in column "Parameters set" indicates that a true parameter has been obtained and stored in the table. An "O" indicates the opposite.

In Table 1 "N" denotes the number of activity or workload levels for which averaged parameter values have been stored and over which the quotient ΔP/ΔV has to be determined.

For determining the quotient $\Delta P/\Delta V$, $\Delta P$ is first created for each indicated activity or workload interval in the table. All pressure data are referenced to the pressure for the patient in rest, Prest. The corresponding process is performed for $\Delta V$. Since N activity or workload intervals are indicated as active in Table 1, N−1 quotients $K_i=\Delta P_i/\Delta V_i$; are obtained. The average value of the $K_i$-values is returned, and $K_{avg}=(\Sigma K_i)/(N-1)$ is obtained. Thus the quotient $K_{avg}$ is calculated.

The quotient $K_{avg}$ is then compared to a predetermined reference value, preferably established and stored at the beginning of the use of the apparatus according to the invention (when the patient possibly were not yet suffering from DHF). By storing subsequent quotients $K_{avg}$ together with associated time marks the evolvement of the degree of DHF can be followed over time. A test can be set up to test whether the quotient has passed a certain limit for starting an automatic transmission of the DHF status of the patient to the physician. This message is transferred by means of the telemetry link of the apparatus according to the invention.

Although modifications and changes may be suggested by those skilled in the art, it is the invention of the inventors to embody within the patent warranted heron all changes and modifications as reasonably and properly come within the scope of their contribution to the art.

I claim:

1. An implantable medical apparatus for detecting diastolic heart failure (DHF), comprising:
    a pressure measuring unit adapted to interact with a living subject to measure an absolute pressure value at a location and time selected from the group consisting of the left atrium during the diastasis phase immediately preceding an atrial contraction, and the pulmonary vein when the pulmonary valve is closed, both for a predetermined workload situation of the subject and a rest situation of the subject for a predetermined workload situation of the subject and for a rest situation of the subject; and
    a calculation unit supplied with said absolute pressure value for said predetermined workload situation and said pressure value for said rest situation, said calculation unit forming a difference, $\Delta P$, between said absolute pressure value for said predetermined workload situation and said absolute pressure value for said rest situation, and comparing said difference $\Delta P$ to a predetermined pressure difference reference value to obtain a comparison result indicative of a DHF state of the heart of the subject.

2. An apparatus as claimed in claim 1, comprising an activity sensor adapted to interact with the subject to detect physical activity of the subject, said activity sensor emitting an activity signal, and a workload calculator supplied with said activity signal that calculates a workload situation of the subject from said activity signal, said workload calculator emitting an output to said calculation unit indicative of said workload situation.

3. An apparatus as claimed in claim 1 wherein said pressure measuring unit measures said absolute value of said pressure at the left atrium during the diastasis phase immediately preceding an atrial contraction, and wherein said apparatus comprises a pressure compensator, supplied with said absolute value of said pressure for said predetermined workload situation and said absolute value of said pressure for said rest situation, that corrects each of said absolute pressure values with a correction value selected from the group consisting of average pressure in the right atrium, and average pressure in the vena cava close to the right atrium.

4. An apparatus as claimed in claim 1 comprising:
    an impedance measuring unit having a first electrode adapted for implantation in the left ventricle of the heart and a second electrode adapted for implantation at a location in a subject at which a substantial portion of variations in impedance occur due to a changing volume of the left ventricle;
    said impedance measuring unit determining a difference $\Delta V$, from respective signals from said first and second electrodes representing an impedance value measured for said predetermined workload situation and an impedance value measured for said rest situation;
    a quotient forming unit that forms a quotient $\Delta P/\Delta V$ and that supplies a signal representing said quotient to said calculation unit; and
    said calculation unit comparing said quotient with a predetermined quotient reference value, as said predetermined pressure difference reference value, to obtain said comparison result.

5. An apparatus as claimed in claim 4 wherein said pressure measuring unit measures said absolute pressure value for each of said predetermined workload situation and said rest situation over a plurality of cardiac cycles, and wherein said apparatus comprises an averaging unit that forms a first average value of said absolute pressure values for said plurality of cardiac cycles for said predetermined workload situation and a second average value of said absolute pressure values for said plurality of cardiac cycles for said rest situation, and wherein said calculation unit forms said difference $\Delta P$ from said first and second average values.

6. An apparatus as claimed in claim 4 wherein said impedance measuring unit measures said impedance value for each of said predetermined workload situation and said rest situation over a plurality of cardiac cycles, and wherein said apparatus comprises an averaging unit that forms a first average value of said impedance values for said plurality of cardiac cycles for said predetermined workload situation and a second average value of said impedance values for said plurality of cardiac cycles for said rest situation, and wherein said calculation unit forms said difference $\Delta V$ from said first and second average values.

7. An apparatus as claimed in claim 1 wherein said pressure measuring unit measures said absolute pressure value for each of said predetermined workload situation and said rest situation over a plurality of cardiac cycles, and wherein said apparatus comprises an averaging unit that forms a first average value of said absolute pressure values for said plurality of cardiac cycles for said predetermined workload situation and a second average value of said absolute pressure values for said plurality of cardiac cycles for said rest situation, and wherein said calculation unit forms said difference $\Delta P$ from said first and second average values.

8. An apparatus as claimed in claim 1 comprising a wireless communication unit connected to said calculation unit that automatically wirelessly transmits said comparison result to an external receiver.

9. An apparatus as claimed in claim 1 comprising a memory connected to said calculation unit that stores said comparison result.

10. An implantable cardiac pacemaker comprising:
    a diastolic heart failure (DHF) determining device comprising a pressure measuring unit adapted to interact with a living subject to measure an absolute pressure value at a location and time selected from the group consisting of the left atrium during the diastasis phase immediately preceding an atrial contraction, and the pulmonary vein when the pulmonary valve is closed, both for a predetermined workload situation of the subject and a rest situation of the subject for a predetermined workload situation of the subject and for a rest situation of the subject, and a calculation unit supplied with said absolute pressure value for said predetermined workload situation and said pressure value for said rest situation, said calculation unit forming a difference, $\Delta P$, between said absolute pressure value for said predetermined workload situation and said absolute pressure value for said rest situation, and comparing said difference $\Delta P$ to a predetermined pressure difference reference value to obtain a comparison result indicative of a DHF state of the heart of the subject; and a therapy administration unit adapted to interact with the heart of the subject to administer electrical cardiac therapy thereto, said therapy administration unit being connected to said DHF determining device, and being supplied with said comparison result, and administering said electrical cardiac therapy dependent on said comparison result.

11. An apparatus as claimed in claim 10, comprising an activity sensor adapted to interact with the subject to detect physical activity of the subject, said activity sensor emitting an activity signal, and a workload calculator supplied with said activity signal that calculates a workload situation of the subject from said activity signal, said workload calculator emitting an output to said calculation unit indicative of said workload situation.

12. A pacemaker as claimed in claim 11 wherein said activity sensor is a pressure sensor.

13. An apparatus as claimed in claim 12 wherein said pressure measuring unit measures said absolute value of said pressure at the left atrium during the diastasis phase immediately preceding an atrial contraction, and wherein said apparatus comprises a pressure compensator, supplied with said absolute value of said pressure for said predetermined workload situation and said absolute value of said pressure for said rest situation, that corrects each of said absolute pressure values with a correction value selected from the group consisting of average pressure in the right atrium, and average pressure in the vena cava close to the right atrium.

14. A method for detecting diastolic heart failure (DHF), comprising the steps of:

measuring an absolute pressure value in vivo in a subject at a location and time selected from the group consisting of the left atrium during the diastasis phase immediately preceding an atrial contraction, and the pulmonary vein when the pulmonary valve is closed, both for a predetermined workload situation of the subject and a rest situation of the subject for a predetermined workload situation of the subject and for a rest situation of the subject; and electronically forming a difference, $\Delta P$, between said absolute pressure value for said predetermined workload situation and said absolute pressure value for said rest situation, and electronically comparing said difference $\Delta P$ to a predetermined pressure difference reference value to obtain a comparison result indicative of a DHF state of the heart of the subject.

15. A method as claimed in claim 14 comprising:

measuring impedance values with a first electrode implanted in the left ventricle of the heart and a second electrode implanted at a location in a subject at which a substantial portion of variations in impedance occur due to a changing volume of the left ventricle;

electronically determining a difference $\Delta V$, from respective signals from said first and second electrodes representing an impedance measured for said predetermined workload situation and an impedance measured for said rest situation;

electronically forming a quotient $\Delta P/\Delta V$; and wherein the step of electronically comparing comprises comparing said quotient with a predetermined quotient reference value, as said predetermined pressure difference reference value, to obtain said comparison result.

16. A method as claimed in claim 15 comprising, in a calibration procedure, measuring instantaneous values of said left ventricular volume with an ultrasound technique and establishing a relation between the ultrasonically measured ventricular values and said impedance values measured simultaneously therewith.

17. A method as claimed in claim 15 comprising measuring said absolute pressure value for each of said predetermined workload situation and said rest situation over a plurality of cardiac cycles, and electronically forming a first average value of said absolute pressure values for said plurality of cardiac cycles for said predetermined workload situation and a second average value of said absolute pressure values for said plurality of cardiac cycles for said rest situation, and electronically forming said difference $\Delta P$ from said first and second average values.

18. A method as claimed in claim 15 comprising measuring said impedance value for each of said predetermined workload situation and said rest situation over a plurality of cardiac cycles, and electronically forming a first average value of said impedance values for said plurality of cardiac cycles for said predetermined workload situation and a second average value of said impedance values for said plurality of cardiac cycles for said rest situation, and electronically forming said difference $\Delta V$ from said first and second average values.

19. A method as claimed in claim 15 comprising measuring said impedance values for said predetermined workload situation of the subject when said subject is not suffering from DHF and determining said reference value therefrom, and measuring said impedance values for said rest situation when said patient is not suffering from DHF and said determining said reference value therefrom.

20. A method as claimed in claim 14 comprising measuring said absolute pressure value for each of said predetermined workload situation and said rest situation over a plurality of cardiac cycles, and electronically forming a first average value of said absolute pressure values for said plurality of cardiac cycles for said predetermined workload situation and a second average value of said absolute pressure values for said plurality of cardiac cycles for said rest situation, and electronically forming said difference $\Delta P$ from said first and second average values.

21. A method as claimed in claim 14 comprising automatically wirelessly transmitting said comparison result to an external receiver.

22. A method as claimed in claim 14 comprising electronically storing said comparison result.

23. A method as claimed in claim 14 comprising measuring said pressure values for said predetermined workload situation of the subject when said subject is not suffering from DHF and determining said reference value therefrom, and measuring said pressure values for said rest situation when said patient is not suffering from DHF and determining said reference value therefrom.

* * * * *